United States Patent [19]

Meyer et al.

[11] 4,161,535
[45] Jul. 17, 1979

[54] PESTICIDAL 2-ISOPROPYL-4-PHENYL-3-BUTENOIC ACID BENZYL ESTERS

[75] Inventors: Willy Meyer, Riehen; Jozef Drabek, Oberwil; Saleem Farooq, Aesch; Laurenz Gsell, Füllinsdorf; Odd Kristiansen, Möhlin, all of Switzerland

[73] Assignee: Ciba-Geigy Corporation, Ardsley, N.Y.

[21] Appl. No.: 836,635

[22] Filed: Sep. 26, 1977

[30] Foreign Application Priority Data

Sep. 30, 1976 [CH] Switzerland ............... 12369/76
Mar. 11, 1977 [CH] Switzerland ............... 3095/77

[51] Int. Cl.² .................. A01n 9/20; A61K 31/275 C07C/121/75
[52] U.S. Cl. ............... 424/304; 260/465 D; 260/544 D; 560/104; 562/495
[58] Field of Search ............ 260/465 D; 424/304

[56] References Cited
U.S. PATENT DOCUMENTS

| 3,666,789 | 5/1972 | Itaya et al. ............... 260/468 |
| 3,835,176 | 9/1974 | Matsuo et al. ............. 260/465 D |
| 3,979,519 | 9/1976 | Punja ........................ 424/304 |
| 3,996,244 | 12/1976 | Fujimoto et al. .......... 260/332.2 A |
| 4,024,163 | 5/1977 | Elliott et al. ............. 260/347.4 |
| 4,031,239 | 6/1977 | Schrider ..................... 424/304 |
| 4,042,710 | 8/1977 | Bull et al. ................... 424/304 |
| 4,058,622 | 11/1977 | Fujimoto et al. ............. 424/308 |

Primary Examiner—Dolph H. Torrence
Attorney, Agent, or Firm—Harry Falber

[57] ABSTRACT

2-Isopropyl-4-phenyl-3-butenoic acid benzyl esters of the formula

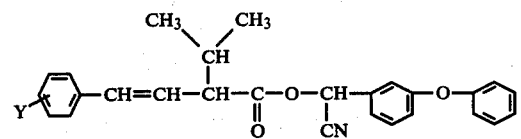

wherein Y is hydrogen, halogen or methyl.

Processes for producing them, and their use in combating pests.

7 Claims, No Drawings

PESTICIDAL 2-ISOPROPYL-4-PHENYL-3-BUTENOIC ACID BENZYL ESTERS

The present invention relates to 2-isopropyl-4-phenyl-3-butenoic acid benzyl esters, to processes for producing them, and to their use in combating pests.

The 2-isopropyl-4-phenyl-3-butenoic acid benzyl esters have the formula

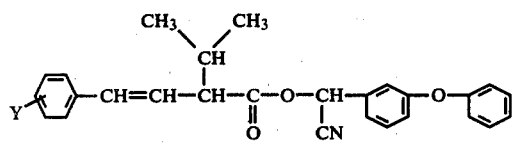

wherein Y is hydrogen, halogen or methyl.

By halogen is meant fluorine, chlorine, bromine or iodine, but especially chlorine.

The compounds of the formula I are produced by methods known per se, for example as follows:

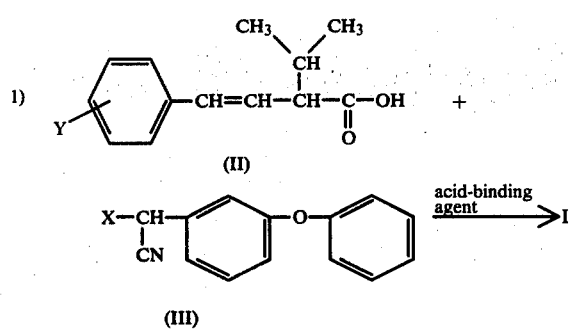

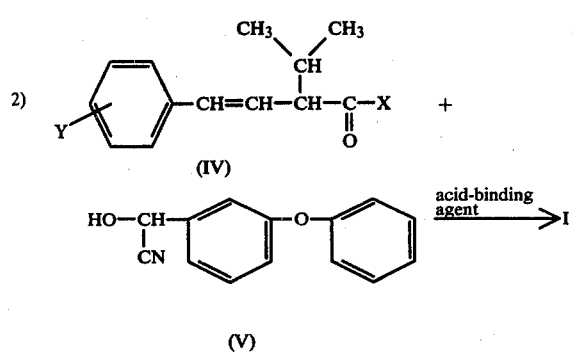

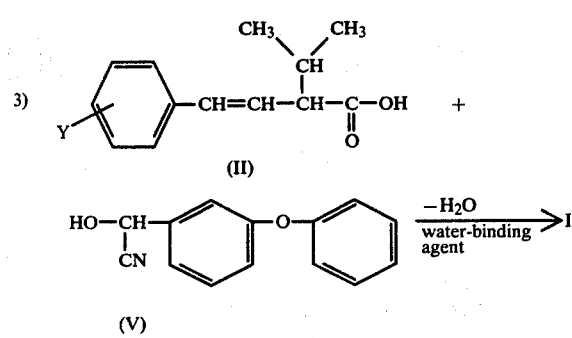

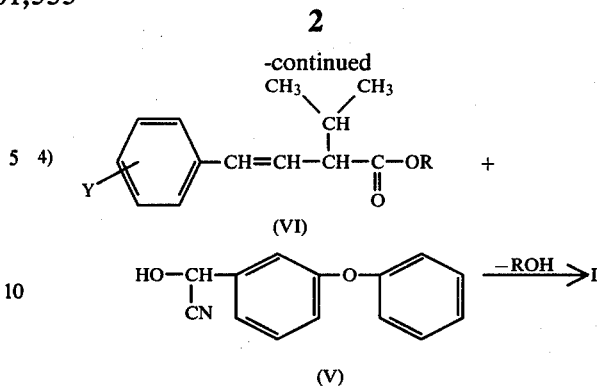

In the formulae II, IV and VI, the symbol Y has the meaning given under the formula I.

In the formulae III and IV, the symbol X denotes a halogen atom, particularly chlorine or bromine; and in the formula VI, R is $C_1$-$C_4$-alkyl, especially methyl or ethyl.

Suitable acid binding agents for the processes 1 and 2 are, in particular, tertiary amines such as trialkylamine and pyridine; also hydroxides, oxides, or carbonates and bicarbonates of alkali metal salts and alkaline-earth metal salts, as well as alkali metal alcoholates such as potassium-t.-butylate and sodium methylate. As water-binding agent for the process 3, it is possible to use, for example, dicyclohexylcarbodiimide. The processes 1 to 4 are performed at a reaction temperature of between $-10°$ and $+120°$ C., preferably between 20° and 80° C., under normal or elevated pressure, and preferably in an inert solvent or diluent. Suitable solvents or diluents are, for example, ethers and ethereal compounds such as diethyl ether, dipropyl ether, dioxane, dimethoxyethane and tetrahydrofuran; amides such as N,N-dialkylated carboxylic acid amides; aliphatic, aromatic and also halogenated hydrocarbons, particularly benzene, toluene, xylene, chloroform and chlorobenzene; nitriles such as acetonitrile; dimethylsulphoxide, and ketones such as acetone and methyl ethyl ketone.

The starting materials of the formulae II to VI are known or can be produced by methods analogous to known methods.

The compounds of the formula I are obtained as mixtures of various optically active isomers, unless the starting materials used to produce the said compounds are homogeneous optically active compounds. The different isomeric mixtures can be separated by known methods into the individual isomers. It is understood that the term 'compounds of the formula I' embraces both the individual isomers and the mixtures thereof.

The compounds of the formula I are suitable for combating various animal and plant pests. These compounds are suitable, in particular, for combating insects, phytopathogenic mites and ticks, for example of the orders: Lepidoptera, Coleoptera, Homoptera, Heteroptera, Diptera, Acarina, Thysanoptera, Orthoptera, Anoplura, Siphonoptera, Mallophage, Thysanura, Isoptera, Psocoptera and Hymenoptera. The compounds of the formula I are especially suitable for combating insects that damage plants, particularly insects that damage plants by eating, in crops of ornamental plants and useful plants, especially in cotton crops (e.g. against *Spodoptera littoralis* and *Heliothis virescens*) and in crops of vegetables (e.g. against *Leptinotarsa decemlineata* and *Myzus persicae*). Active substance of the formula I also have a very good action against flies, such as *Musca domestica*, and against mosquito larvae.

The acaricidal and insecticidal action can be substantially broadened and adapted to suit given circumstances by the addition of other insecticides and/or acaricides. Suitable additives are, for example, organic phosphorus compounds; nitrophenols and derivatives thereof; formamidines; ureas; other pyrethrin-like compounds; and also carbamates and chlorinated hydrocarbons.

Compounds of the formula I are combined particularly advantageously also with substances which have a synergistic or intensifying effect on pyrethroids. Examples of such compounds are, inter alia, piperonylbutoxide, propynyl ethers, propynyl oximes, propynyl carbamates and propynyl phosphonates, 2-(3,4-methylenedioxyphenoxy)-3,6,9-trioxaundecane (Sesamex or Sesoxane), S,S,S-tributylphosphorotrithioates and 1,2-methylenedioxy-4-(2-(octylsulphonyl)-propyl)-benzene.

Compounds of the formula I can be used on their own or together with suitable carriers and/or additives. Suitable additives can be solid or liquid and they correspond to the substances common in formulation practice, such as natural or regenerated substances, solvents, dispersing agents, wetting agents, adhesives, thickeners, binders and/or fertilisers.

The compositions according to the invention are produced in a manner known per se by the intimate mixing and/or grinding of active substances of the formula I with suitable carriers, optionally with the addition of dispersing agents or solvents which are inert to the active substances. The active substances can be obtained and used in the following forms:

Solid Preparations: dusts, scattering agents, granulates (coated granulates, impregnated granulates and homogeneous granulates);

Liquid Preparations:
 (a) water-dispersible concentrates of active substance: wettable powders, pastes or emulsions;
 (b) solutions.

The content of active substance in the described compositions is between 0.1 and 95%; in this respect it is to be mentioned that in the case of application from an aeroplane, or by means of other suitable devices, concentrations of up to 99.5% or even the pure active substance can be used.

The active substances of the formula I can be formulated for example as follows (parts are by weight):

Dusts:
The following substances are used to produce (a) a 5% dust and (b) a 2% dust;
 (a)
  5 parts of active substance,
  95 parts of talcum;
 (b)
  2 parts of active substance,
  1 part of highly dispersed silicic acid,
  97 parts of talcum.
The active substances are mixed and ground with the carriers.

Granulate:
The following substances are used to produce a 5% granulate:
 5 parts of active substance,
 0.25 part of epichlorohydrin,
 0.25 part of cetyl polyglycol ether,
 3.50 parts of polyethylene glycol,
 91 parts of kaolin (particle size 0.3–0.8 mm).

The active substance is mixed with epichlorohydrin and dissolved with 6 parts of acetone; the polyethylene glycol and cetyl polyglycol ether are then added. The solution obtained is sprayed onto kaolin, and the acetone is then evaporated off in vacuo.

Wettable Powder:
The following constituents are used to produce (a) a 40%, (b) and (c) a 25%, and (d) a 10% wettable powder:
 (a)
  40 parts of active substance,
  5 parts of sodium lignin sulphonate,
  1 part of sodium dibutyl-naphthalene sulphonate,
  54 parts of silicic acid;
 (b)
  25 parts of active substance,
  4.5 parts of calcium lignin sulphonate,
  1.9 parts of Champagne chalk/hydroxyethyl cellulose mixture (1:1),
  1.5 parts of sodium dibutyl-naphthalene sulphonate,
  19.5 parts of silicic acid,
  19.5 parts of Champagne chalk,
  28.1 parts of kaolin;
 (c)
  25 parts of active substance,
  2.5 parts of isooctylphenoxy-polyoxyethylene-ethanol,
  1.7 parts of Champagne chalk/hydroxyethyl cellulose mixture (1:1),
  8.3 parts of sodium aluminium silicate,
  16.5 parts of kieselguhr,
  46 parts of kaolin;
 (d)
  10 parts of active substance,
  3 parts of a mixture of the sodium salts of saturated fatty alcohol sulphates,
  5 parts of naphthalenesulphonic acid/formaldehyde condensate,
  82 parts of kaolin.

The active substance is intimately mixed in suitable mixers with the additives, and the mixture is then ground in the appropriate mills and rollers. Wettable powders are obtained which can be diluted with water to give suspensions of the desired concentration.

Emulsifiable Concentrates:
The following substances are used to produce (a) a 10%, (b) a 25%, and (c) a 50% emulsifiable concentrate:
 (a)
  10 parts of active substance,
  3.4 parts of epoxidised vegetable oil,
  3.4 parts of a combination emulsifier consisting of fatty alcohol polyglycol ether and alkylarylsulphonate calcium salt,
  40 parts of dimethylformamide,
  43.2 parts of xylene;
 (b)
  25 parts of active substance,
  2.5 parts of epoxidised vegetable oil,
  10 parts of alkylarylsulphonate/fatty alcohol polyglycol ether mixture,
  5 parts of dimethylformamide,
  57.5 parts of xylene;

(c)
  50 parts of active substance,
  4.2 parts of tributylphenol-polyglycol ether,
  5.8 parts of calcium-dodecylbenzenesulphonate,
  20 parts of cyclohexanone,
  20 parts of xylene.

Emulsions of the desired concentration can be prepared from these concentrates by dilution with water.

Spray:

The following constituents are used to produce (a) a 5% spray and (b) a 95% spray:
(a)
  5 parts of active substance,
  1 part of epichlorohydrin,
  94 parts of ligroin (boiling limits 160°14 190° C.);
(b)
  95 parts of active substance,
  5 parts of epichlorohydrin.

The invention is further illustrated by the following Examples.

EXAMPLE 1

Production of 2-isopropyl-4-phenyl-3-butenoic acid-α-cyano-m-phenoxybenzyl ester (a) 1.5 g of sodium hydride (3.8 g of a dispersion in oil) is heated in 60 ml of dimethylsulphoxide at 70°-75° C. for 1.5 hours until there is no further escape of hydrogen. To the solution, cooled to 20°-25° C., is added 7.8 g of 4-phenyl-3-butenoic acid ethyl ester. Alkylation is then performed at 15°-20° C. with 7.4 g of isopropyl bromide, and the reaction mixture is subsequently stirred at 40° C. for two hours; water is then added and extraction is repeatedly performed with ethyl acetate. After concentration by evaporation, the product is chromatographed through silica gel with toluene to obtain the compound of the formula

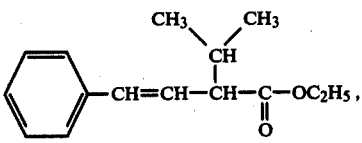

which can be further processed without additional purification.

(b) A solution of 3.5 g of 2-isopropyl-4-phenyl-3-butenoic acid ethyl ester, 10 g of 85% KOH, 30 ml of ethanol and 5 ml of water is stirred at 80° C. for 15 hours. The solution is then completely concentrated; water is added and washing is performed with a small amount of ethyl acetate. After acidification, subsequent extraction and drying, the reaction mixture is refluxed with 1.8 g of thionyl chloride in 30 ml of absolute toluene, with stirring, for 12 hours. Concentration by evaporation yields 2-isopropyl-4-phenyl-3-butenoic acid chloride, which is further processed in the crude form.

(c) 1.2 g of pyridine is added dropwise at 20°-25° C. to 2.8 g of 2-isopropyl-4-phenyl-3-butenoic acid chloride and 2.84 g of m-phenoxymandelic acid nitrile in 40 ml of toluene. Stirring is subsequently maintained for 12 hours at 20° C., and extraction is then performed once with diluted hydrochloric acid and three times with water. After drying and concentration by evaporation, there remains the compound of the formula

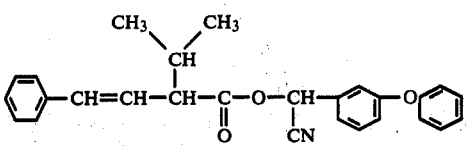

having a refractive index of $n_D^{21°} = 1.573$.

The following compounds are produced in an analogous manner:

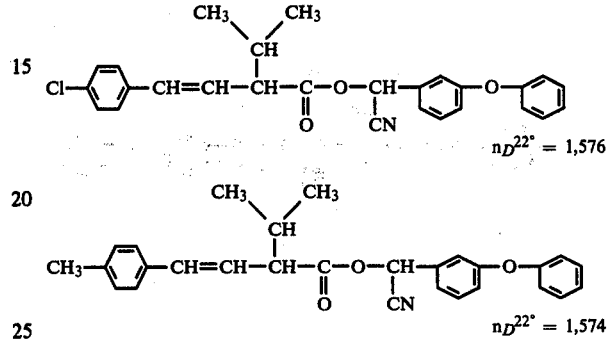

$n_D^{22°} = 1,576$ $n_D^{22°} = 1,574$

EXAMPLE 2

(A) Insecticidal stomach-poison action

Cotton plants were sprayed with a 0.05% aqueous emulsion of the active substance (obtained from a 10% emulsifiable concentrate).

After drying of the coating, larvae of *Spodoptera littoralis* in the L$_3$ stage and of *Heliothis virescens* in the L$_3$ stage were placed onto the cottom plants. The test was carried out at 24° C. with 60% relative humidity.

Compounds according to Example 1 exhibited in the above test a good insecticidal stomach-poison action against larvae of *Spodoptera littoralis* and *Heliothis virescens*.

(B) Systemic insecticidal action

In order to determine the systemic action, rooted bean plants (*Vicia faba*) were placed into a 0.01% aqueous solution of the active substance (obtained from a 10% emulsifiable concentrate). After 24 hours, bean aphids (*Aphis fabae*) were placed onto the parts of the plants that had been above the soil. By means of a special device, the bean aphids were protected from the effects of contact and of gas. The test was carried out at 24° C. with 70% relative humidity.

Compounds according to Example 1 exhibited in the above test a systemic insecticidal action against *Aphis fabae*.

We claim:

1. A compound of the formula

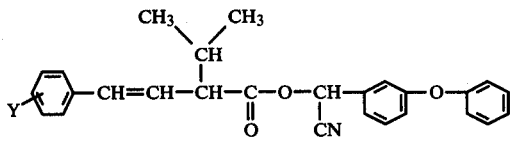

wherein Y is hydrogen, halogen or methyl.

2. The compound according to claim 1, of the formula

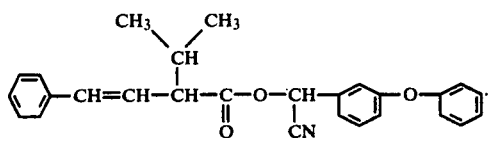

3. The compound according to claim 1, of the formula

4. The compound according to claim 1, of the formula

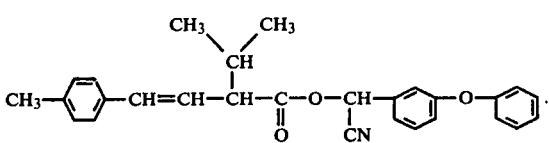

5. A pesticidal composition which comprises a pesticidally effective amount of a compound according to claim 1 as active ingredient, and suitable carriers therefor.

6. A method of combatting animal and plant pests at a locus, which method comprises applying to the locus a pesticidally effective amount of a compound as claimed in claim 1.

7. A method according to claim 6 wherein the pests are of the class Insecta.

* * * * *